US009207163B2

(12) United States Patent
Shiraishi et al.

(10) Patent No.: US 9,207,163 B2
(45) Date of Patent: Dec. 8, 2015

(54) GLASS-CELL VIAL FOR EXAMINING SLIGHT AMOUNT OF SPECIMEN

(75) Inventors: Hiromi Shiraishi, Osaka (JP); Haruki Oishi, Osaka (JP); Kazuto Shiotani, Toyonaka (JP); Kazuhiro Mori, Takarazuka (JP); Jun Mutoh, Kobe (JP)

(73) Assignees: WAKO PURE CHEMICAL INDUSTRIES, LTD., Osaka-shi (JP); SHIOTANI M.S. CO., LTD., Amagasaki-shi (JP)

( * ) Notice: Subject to any disclaimer, the term of this patent is extended or adjusted under 35 U.S.C. 154(b) by 1175 days.

(21) Appl. No.: 12/596,749

(22) PCT Filed: Mar. 24, 2008

(86) PCT No.: PCT/JP2008/055366
§ 371 (c)(1),
(2), (4) Date: Jan. 19, 2010

(87) PCT Pub. No.: WO2008/132905
PCT Pub. Date: Nov. 6, 2008

(65) Prior Publication Data
US 2010/0136601 A1 Jun. 3, 2010

(30) Foreign Application Priority Data
Apr. 20, 2007 (JP) ................. 2007-112020

(51) Int. Cl.
*C03B 9/00* (2006.01)
*G01N 21/03* (2006.01)
*G01N 21/15* (2006.01)

(52) U.S. Cl.
CPC ............. *G01N 21/03* (2013.01); *G01N 21/15* (2013.01); *G01N 2021/0378* (2013.01)

(58) Field of Classification Search
CPC .......... G01N 2021/0378; G01N 21/03; G01N 21/15; G01N 2021/151; G01N 2021/03

USPC ............... 65/276, 280, 108, 109, 110
See application file for complete search history.

(56) References Cited

U.S. PATENT DOCUMENTS 2,159,736 A * 5/1939 Geiger et al. ............... 65/109
2,273,777 A * 2/1942 Berthold ..................... 65/76

FOREIGN PATENT DOCUMENTS

| JP | 1-131459 | 5/1989 |
|---|---|---|
| JP | 7-20037 | 1/1995 |

(Continued)

OTHER PUBLICATIONS

International Search Report for International Application No. PCT/JP2008/055366 dated Apr. 30, 2008.

*Primary Examiner* — Richard Crispino
*Assistant Examiner* — Yana B Krinker
(74) *Attorney, Agent, or Firm* — Kratz, Quintos & Hanson, LLP

(57) ABSTRACT

A glass-cell vial is provided which can examine specimen without causing any hindrance even when as minimum as possible specimen is used, and prevents mixture of foreign substances from causing examination errors.

A vial is provided which comprises function of cell capable of optical examination, and the inner surface of bottom of the vial is formed to be a round-state convex part upwardly and the outer surface of the bottom is formed to be in convex state. When a small amount of liquid specimen is introduced into this cell vial, a part which can be a light irradiation part for optical examination can be positioned between the meniscus part of the liquid specimen and the upper end of the inner bottom. Consequently, it becomes possible to examine light quantity variation even though the specimen is in small amount.

3 Claims, 4 Drawing Sheets

(56) References Cited

FOREIGN PATENT DOCUMENTS

| JP | 8-43400 | 2/1996 |
|---|---|---|
| JP | 2000-19099 | 1/2000 |
| JP | 2005-41744 A1 | 2/2005 |
| JP | 2005-47750 A1 | 2/2005 |
| WO | WO 99/13986 A1 | 3/1999 |
| WO | WO 2007/013254 A1 | 2/2007 |

\* cited by examiner (A)

INNER DIAMETER A

THICKNESS B (B)

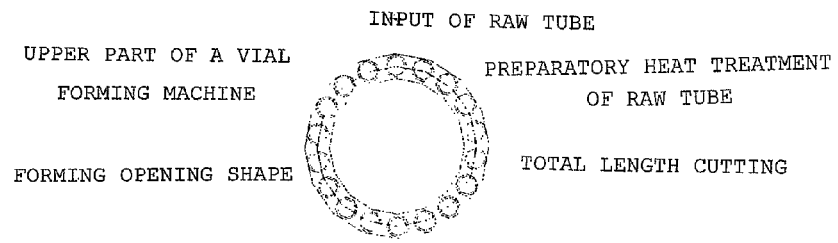

UPPER PART OF A VIAL FORMING MACHINE

INPUT OF RAW TUBE
PREPARATORY HEAT TREATMENT OF RAW TUBE
TOTAL LENGTH CUTTING
FORMING OPENING SHAPE (B)

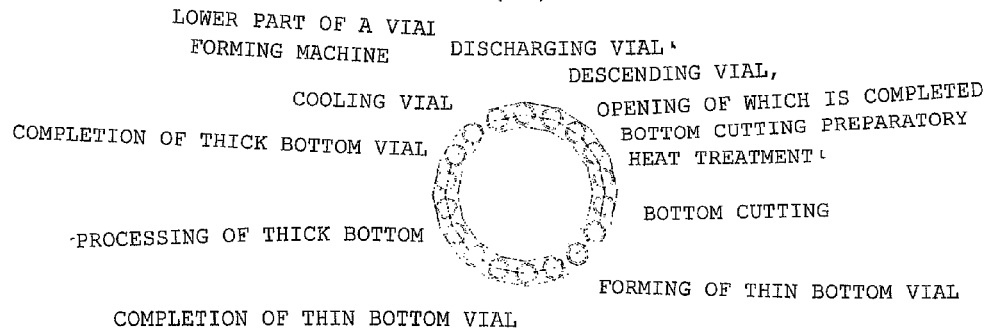

LOWER PART OF A VIAL FORMING MACHINE
DISCHARGING VIAL
DESCENDING VIAL,
COOLING VIAL
OPENING OF WHICH IS COMPLETED
COMPLETION OF THICK BOTTOM VIAL
BOTTOM CUTTING PREPARATORY HEAT TREATMENT
BOTTOM CUTTING
-PROCESSING OF THICK BOTTOM
FORMING OF THIN BOTTOM VIAL
COMPLETION OF THIN BOTTOM VIAL

GLASS-CELL VIAL FOR EXAMINING SLIGHT AMOUNT OF SPECIMEN

TECHNICAL FIELD

The present invention relates to a glass-cell vial which is a vial having a reagent (examination agent) holding function furnished with the function of an optically measuring cell, and more particularly, to a glass-cell vial which allows secure and easy examination of a small amount of a specimen and a examination reagent; a manufacturing method thereof; and a measuring method of light quantity variations using the cell vial.

BACKGROUND ART

It has been an obligation for pharmaceutical manufacturing that every production lot is subjected to endotoxin test. Furthermore, it has been a general technical knowledge that a medical implement and a cell-culturing apparatus also should be managed in terms of endotoxin. The present invention facilitates secure completion of such a test for even a small amount of a specimen, allowing reduction in amount of the specimen to test and an examination reagent to use.

A specimen is generally measured with a reagent (examination agent) after the reagent is manually transferred from the holding bottle to a cell. However, this manual procedure is inevitably accompanied by many troubles such as a scattering of reagent, a contaminating foreign substance, and an inaccurately weighed reagent. Thus, in recently increasing manners, the reagent is automatically transferred into the cell. Alternatively, a cell vial has been known to allow an examination that is free from transferring the reagent into the cell and can be simply completed by putting the specimen into the vial with the reagent held in beforehand.

Meanwhile, the endotoxin test for every production lot of a specimen medicine has been conventionally carried out by a pyrogen test in which a test rabbit is administered in vivo with the specimen medicine to monitor daily the change in body temperature. However, to confirm the test result needs 2-3 days up to a lifted temperature and an amount of the specimen as much as 20,000 μl to 50,000 μl and is accompanied by the problem of lacking reliability. Additionally, the test has a problem that it costs too much due to the fed rabbit and the observation labor after administration.

Recently, the endotoxin test has been quickly and securely carried out by utilizing a method in which a hemocyte component-containing solution from a horseshoe crab (hereinafter, abbreviated to an AL solution) is reacted with endotoxin to give an enzyme (such as protease), of which the activation reaction or the coagulation is then used as a base to measure an endotoxin concentration in the specimen. Furthermore, in order to automatically confirm the gelation reaction, an instrument such as a toxinometer (made by Wako Pure Chemical Industries, Ltd.) has been developed to facilitate a toxicity test. The toxinometer is generally used to examine a specimen by a method in which a light emitting diode is used irradiate light to the flat part (the straight part, in other words, the problem-free part for optical measurement) in the side surface of a vial with the specimen held in.

Conventionally, glass vial has been produced by such method as: a blowing method in which a lump of glass poured from melting vessel is shut in a separable molding die and air pressure forms the shape; a horizontal method in which a raw material tube elongated in perfect circle is laid in transversal position to be processed; and a vertical method in which a raw material tube is placed in upright position to be processed.

However, there has been only horizontal method conventionally for making a bottom part to be thick.

That is, in order to make the bottom part to be thick, it was necessary that a vial with thin bottom was formed in a vertical method, and thereafter the bottom part was to be burnt in a horizontal method. In other words, conventional method was two processes method which required position change of a vial, that is, thin bottom was formed in a vertical method and then the bottom part was made to be thick in a horizontal method.

In addition, since the above mentioned conventional method utilizes horizontal method, the shape of inner plane of thick bottom vial could be formed to be convex round state only in downward direction.

FIG. 1(A) shows a conventional manufacturing method of another vial. A slender pipe is held upright placing the bottle opening in upward position, the lowest end opening thereof is heated to be melt while the pipe is rotating, and compressed air is blown from the bottle opening, so that bottom part of the bottle is formed. A vial which is formed in this way has such configuration that, as shown in FIG. 2(A), both of the inner surface and the outer surface of the bottom is formed in a shape protruding downwardly in round state.

When liquid specimen is poured into a vial obtained by these conventional manufacturing methods, the light irradiated at the bottom part is distorted as the bottom part is formed to be round. Consequently, the light has to be irradiated in a smooth part (a straight part, in other words a part which has no hindrance for optical measurement). For that reason, there have been such problems as the position of light irradiation had to be in a position as high as possible from the bottom, and the amount of specimen was required as much as 1,000 to 2,000 μl at least to secure a lighting position without any hindrance for examination due to generation of meniscus at the upper surface of the liquid due to surface tension. Whereby, there has been such a problem that the amount of reagent usage is required in large quantity.

Moreover, there was a risk of examination error due to hindrance at the optical examination (measurement) caused by contamination of foreign substances when transferring endotoxin examination reagent into examination cell.

DISCLOSURE OF THE INVENTION

Problems to be Solved by the Invention

In the present invention, the invention has been accomplished focusing on the above points and seeks to provide a glass-cell vial which enables to perform optical examination of a specimen without any hindrance even with the practically smallest amount of specimen, and at the same time which prevents contamination of foreign substances so that examination error does not occur.

The invention also seeks to provide a manufacturing method which can manufacture the above glass-cell vial easily, with cheap cost, and with good reproducibility.

Further, the invention seeks to provide an examination method of light quantity variation using the above glass-cell vial.

Means for Solving the Problems

In order to achieve the above objectives, the inventors of the present invention have eagerly studied and resultantly found a fact that when the shape of the bottom part of a glass-cell vial is formed so that the inner surface is a round-state convex part upwardly and the outer surface is in a convex state downwardly, preferably both of the inner and outer bottom are formed to be a convex lens-like shape of a round-state convex parts, the objective optical examination (measurement) is ensured to be realized without any hindrance even with small amount of specimen, and thus the present invention has been achieved.

That is, the present invention provides a vial which contains reagent with function of a cell which is capable of performing optical examination, through arranging to form so that the inner surface of the vial bottom part is a round-state convex part upwardly and the outer surface is in a convex state downwardly, preferably both of the inner and outer bottom are formed to be a convex lens-like shape of a round-state convex parts, and thus, a part that can be a light irradiation part for optical examination can be positioned between the meniscus part of the liquid specimen and the top end of the bottom even when a small amount of liquid specimen is introduced into this cell vial, and such a structure has been achieved that the light can pass through the liquid specimen via the part. Note that the part that can be the light irradiation part is equivalent to the straight part.

It is especially preferable that when the outer surface of the bottom of the cell vial is formed to be a round-state convex part downwardly, the objective cell vial can be manufactured more easily. A cell vial which has convex shape both in inner bottom part and outer bottom part, having no stand alone characteristic, has not been known so far to the general public as far as the applicant knows. This is because a cell vial is easy to handle if it is stored in upright position when freezing to dry the reagent or reserving to use the reagent.

Inner diameter of the cell vial according to the present invention is preferably 4.0 mm to 20.0 mm, and radius of the round-state convex part in the inner bottom is preferably 50 mm to 3.5 mm.

The thickness of the maximum bottom part of the cell vial according to the present invention is preferably in the range of 1:0.2 to 1:0.35 in terms of ratio of inner diameter of the vial to the thickness of bottom of the maximum part. The capacity of the cell vial is preferably 3 to 30 ml approximately. Further, the part which can be the light irradiation part is preferably positioned at 2.5 to 3.5 mm in height from the outer bottom of the cell vial.

Inventors of the present invention studied eagerly the manufacturing method of the cell vial, and resultantly has found a fact that, a glass tube is held in vertical way so that a part becoming the bottom is placed at upper part and the tube is melt, compressed air is blown in from the lower inner surface to form the bottom of bottle at the inner surface of the bottom, thereafter compressed air pressure is varied and owing to the empty weight of the bottom of bottle and blowing control of the compressed air, such a cell vial can be obtained that the inner surface of the bottom is formed to be a round-state convex part upwardly and outer surface is formed in convex state downwardly (the state of convex lens).

A manufacturing method of a glass-cell vial, comprising the steps of:
holding a slender sleeve-like glass tube formed with a bottle opening at lower end in the upright state;
heating an upper end with keeping blow-in of compressed air from the bottle opening at the lower end and rotation of the sleeve-like glass tube to melt by a burner;
collecting melted glass at central part to form the bottom to be in convex state upwardly or downwardly; and
after the steps above, varying the compressed air pressure so that inner surface of the bottom of the vial is formed to be a round-state convex part in a direction toward the bottle opening, and outer surface of the bottom of the vial is formed to be in convex state in an opposite direction to the above. In this case, the shape of the bottle opening is not specifically limited, and simply rounded shape as a general test tube for example, or the one formed to have suitable steps so that cap seal made of aluminum can be fit, may be adapted.

It is preferable that the manufacturing method of the present invention comprises the two steps of:
manufacturing a cell vial having thin bottom by collecting melted glass at the central part as a first step; and
subsequently, heating again by a burner to melt to form a thick bottom cell vial so that the inner surface of the bottom of the vial is a round-state convex part in the direction toward the bottle opening, and the outer surface of the bottom of the vial is in convex state in the opposite direction to the above as a second step (to be convex in both the upward and downward directions).

It is preferable that a cell vial of the present invent ion comprises the step of forming the outer surface of the bottom to be a round-state convex part downwardly, because the objective cell vial can be manufactured easily.

An examination method of light quantity variation of specimen of the invention, comprising the steps of:
adding a small amount of liquid specimen in a glass-cell vial containing a small amount of reagent, for example, in powder or in freeze-dried state to dissolve the reagent;
holding the glass-cell vial in a cell vial holding part of an apparatus;
raising liquid plane position of the liquid specimen by inner round-state convex state part of bottom and outer convex state part of bottom of the cell vial to position a part which can be a light irradiation part for optical examination between upper-most part of the inner round-state convex state part of bottom and meniscus part of upper end of the specimen; and
irradiating with light the light irradiation part to examine light quantity variation of opposite direction to irradiation side (for example, light penetration quantity, light absorbance, scattering light intensity, and the like).

Quantity of the liquid specimen is preferably 100 µl to 300 µl, and the part which can be a light irradiation part is preferable positioned at the height of 2.5 to 3.5 mm from the outer bottom of the cell vial.

Effect of the Invention

According to the present invention, forming inner surface of bottom part of cell vial to be a round-state convex part in the upward direction and outer surface to be in convex state in the downward direction enables meniscus position of liquid specimen to elevate, which makes possible to perform objective optical examination without any hindrance even in a case where small amount of liquid specimen is poured, thereby consumption of reagent and specimen can be remarkably reduced. In addition, in the present invention, the vial containing, for example, freeze-dried reagent or powder and the like is used as a cell as it is, which prevents mixture of foreign substances and examination error due to mixture of foreign substances can be avoided.

Specifically, owing to the fact that meniscus position could be raised, the total liquid quantity in examination (total liquid quantity of reagent and specimen) could be reduced as less as 200 µl to carry out examination. That is to say, for example, in a case where examination is performed in such a way that specimen is added to freeze-dried reagent to dissolve the specimen, the specimen quantity was reduced down to one fifth to one tenth compared with the conventional art, as well as reagent quantity required for examination was reduced to one fifth to one tenth. In short, small amount of specimen and reagent is required, whereby large scale of cost reduction was achieved.

BRIEF DESCRIPTION OF THE DRAWINGS

FIG. 4 shows manufacturing process using a vial forming machine for a cell vial according to the present invention, and in which FIG. 4(A) shows the upper part of the vial forming machine, FIG. 4(B) is a schematic plan view showing manufacturing process in the lower part of the vial farming machine.

BEST MODES FOR CARRYING OUT THE INVENTION

Manufacturing method of a glass-cell vial according to the present invention includes the following processes.

(1) A raw tube (glass material: borosilicate glass), which is produced by a conventional method, having internal diameter of 4.0 mm to 20 mm, preferably 8.0 mm to 15 mm and a thickness of 0.6 mm to 2.4 mm, preferably 0.8 mm to 1.8 mm, is cut into a predetermined length to form a suitable bottle opening depending on necessity by a conventional method, and a slender sleeve-like glass tube is obtained.

Figure 1:
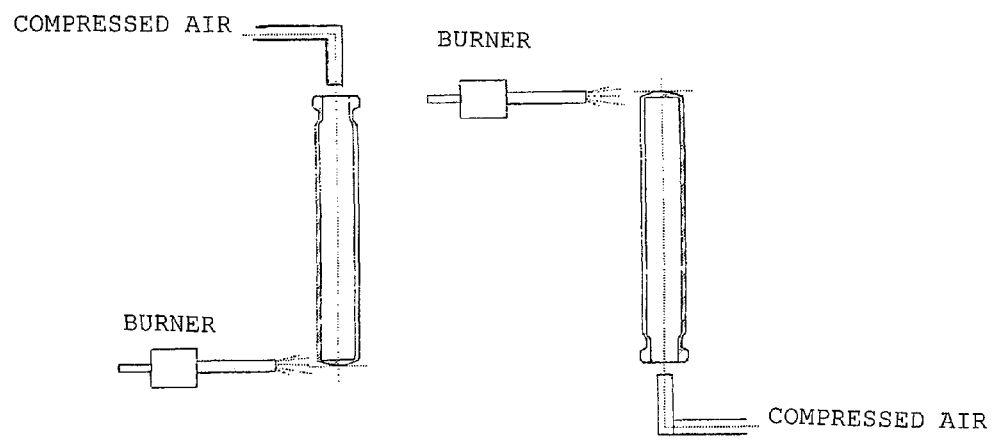
FIG. 1(A) is a schematic sectional view showing manufacturing method of a conventional cell vial.
FIG. 1(B) is a schematic sectional view showing manufacturing method of a cell vial according to the present invention.

(2) As shown in FIG. 1(B), the slender sleeve-like glass tube is held upright having the bottle opening at low end in rotation-free state.

(3) While rotating the sleeve-like glass tube, the top end part is heated by a burner to melt blowing in compressed air from the lower end bottle opening, to collect melted glass at the central part and form a bottle bottom having a thick in central part so that the inner bottom plane is a round-state convex part downwardly (in the direction toward bottle opening). Temperature of the burner is preferably set at 1,200° C. to 1,500° C. Blow-in pressure is preferably regulated by a pressure reducing valve in the range of 3 kg pressure/$cm^2$±1.0 kg pressure/$cm^2$, depending on melting situation of the vial glass.

(4) After forming the bottom of bottle in a predetermined thickness, the compressed air pressure is raised slightly to form the outer surface of the bottom to be a round-state convex part upwardly (in the opposed direction to the bottle opening). It is preferable to apply higher pressure after forming the bottom of bottle than the pressure before forming the bottom of bottle in the range of the above mentioned pressure. It is preferable to set the pressure at 2 to 3 kg pressure/$cm^2$ as pressure until forming the bottom of bottle and set the pressure at 3 to 4 kg pressure/$cm^2$ for forming the outer surface of the bottom to be a round-state convex part.

Note that it is also possible to set the pressure higher at the beginning to form the outer bottom plate to be a round-like convex part in the opposed direction toward the bottle opening and then the pressure is deceased to form the inner bottom plane to be a round-like convex part in the direction toward the bottle opening.

(5) Thereafter, the compressed air is applied to the bottom of bottle from outside. Thus, a vial having the capacity of preferably 3 to 10 ml, more preferably 4 to 6 ml can be obtained.

Figure 3:
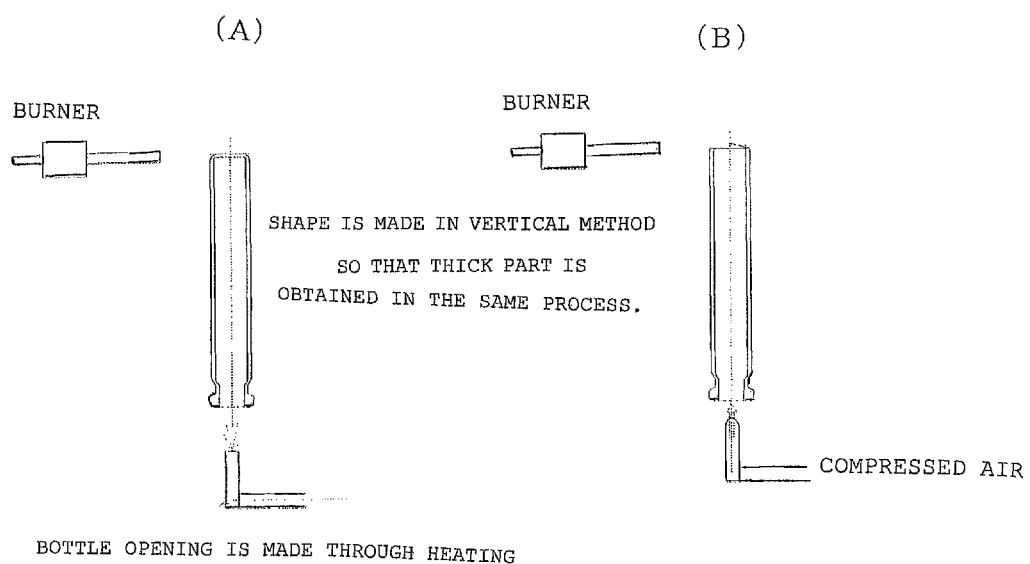
FIG. 3(A) is a schematic sectional view showing manufacturing process of a bottle opening according to the present invention.
FIG. 3(B) is a schematic sectional view showing manufacturing process of lens-like bottom part.

FIG. 3 and FIG. 4 show one example of manufacturing a glass-cell vial according to the present invention using a vertical type vial forming machine consisting of an upper part and a lower part, and FIG. 4(A) shows the manufacturing process in the upper part of the vial forming machine while FIG. 4 (B) shows the same in the lower part thereof.

As shown in FIG. 4(A), raw tubes are installed in the upper part of the forming machine, which is rotated to move intermittently, passing the station to perform preparatory heat treatment of raw tubes and total length cutting, getting to the opening shape forming station, and the opening is formed, as shown in FIG. 3(A), by heating the lower end with a burner.

Thereafter, as shown in FIG. 4(B), the vial, the opening part of which is completed in forming in the upper part, is lowered to the lower part of the forming machine. While the vial itself is rotated to move intermittently, passing the respective station of preparatory heat treatment for bottom cutting and bottom cutting itself, getting to the station of a thin bottom vial forming. In this thin bottom vial forming station, as shown in FIG. 3(B), while the vial is rotating, compressed air is introduced from the lower end opening and the upper end is heated to melt by a burner. Thus, a thin bottom vial is formed and cooled while rotating to move so that a thin bottom vial is achieved, getting to a thick bottom forming station. In the thick bottom forming station, as shown in FIG. 3(B), the vial is heated again to melt by a burner to form a thick bottom vial so as to have a lens-like section, which is cooled through rotation movement to achieve a thick bottom vial. Furthermore, intermittent rotation movement is performed to cool the vial, and then the vial is discharged.

Note that the term "thin bottom" means a bottom having an equivalent thickness to the raw tube thickness (thickness of outer peripheral) which is used for vial farming, and the term "thick bottom" stands for a thickness of 1.3 to 2 times thicker, preferably 1.4 to 1.6 times thicker compared with the thickness of the "thin bottom".

Figure 2:
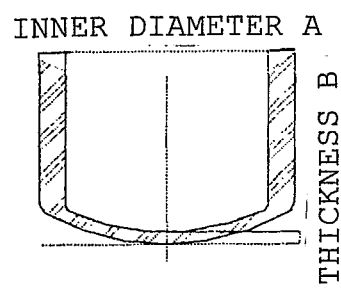
FIG. 2(A) is a sectional view of bottom part of a conventional cell vial.
FIG. 2(B) is a sectional view of a cell vial according to the present invention.
Figure 2:
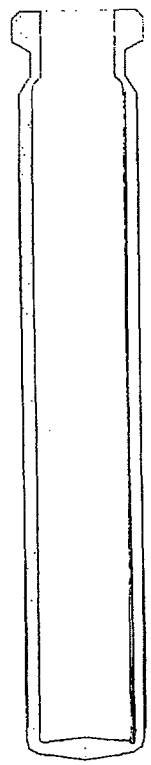

In conventional usual vial, as shown in FIG. 2(A), the ratio of the internal diameter of a vial to the maximum bottom thickness is in the range of 1:0.5 to 1:0.12, and both of the inner and outer surface of the bottom is formed to be a shape protruding downward, whereby when the light irradiation position for optical examination (substantially 3 mm above from the lower end of the bottom of the cell vial) is arranged to be placed in the straight part of vial (circle section part of sleeve state) under the meniscus part of the upper end of the specimen, such a problem has been occurred as a large amount of liquid specimen was required.

In the present invention, as shown in FIG. 2(B), a bottom of convex lens state is formed, hence the light irradiation position (substantially 2.5 mm to 3.5 mm from the lower end) may be placed at a slightly above the upper end of the inner bottom plane (straight part of the vial) and therefore, the required amount of liquid specimen is small. Just for additional remarks, the cell vial according to the present invention is characterized in that a straight part is provided which is suitable as a light irradiation position at substantially 2.5 mm to 3.5 mm from the lower end of the bottom.

The inner diameter of the cell vial according to the present invention is preferably 4.0 mm to 20.0 mm from an aspect of adaptability to examination apparatus in the market.

The radius of the round-state convex part of the inner bottom varies depending on the inner diameter of the vial, but in general, a radius is suitably selected from the range of 50 mm to 3.5 mm, preferably 30 mm to 8 mm. Too small radius is not only difficult to manufacture but also gives smaller range that allows optical examination, and too large radius which is close to flat is not only difficult to manufacture but also the part which is close to flat is hardly to be a straight part (in other words a part without hindrance to perform optical examination), the upper part thereof has to be arranged for the light irradiation position and thereby no specific advantage is obtained.

In the case where the outer bottom is formed to be a round-state convex part, the radius varies depending on the outer diameter of the vial, but in general a radius is suitably selected from the range of 50 to 2.5 mm, preferably 40 to 5 mm, more preferably 30 to 10 mm.

The maximum thickness of the bottom part of the cell vial according to the present invention is preferably, as a ratio of the internal diameter of a vial to the maximum bottom thickness, is in the range of 1:0.2 to 1:0.35. Owing to this arrangement, the radius can be arranged to be in the above radius range.

The cell vial according to the present invention is characterized in that the inner surface of the bottom is formed to be a round-state convex part upwardly and the outer surface is formed to be in convex state downwardly, if the shape is formed to be otherwise, such a vial that has thick bottom and the inner surface is in convex state so that no distortion is generated as well as with less expensive price cannot be obtained.

It is possible to raise the cell vial by putting a suitable thickness plate thereunder using a conventional cell vial which has a flat lower end, which causes the product quality control of the plate which has suitable thickness in addition to the cell vial. It is considerably troublesome and unreasonable practically.

The cell vial formed as described so far is filled or filled to freeze and dried with a small quantity of reagent to provide in the market to sell as a cell vial containing reagent. Such cell vial reduces usage of reagent and decreases the total amount of liquid in examination as well as assuring measurement and safety.

In addition, inventors of the present invention have discovered at the first time that the manufacturing method of the present invention can succeed in obtaining an objective cell vial in less expensive price and with good reproducibility.

In order to examine light quantity variation using the above cell vial, suitable amount of liquid specimen is added to a glass cell-vial which contains a small amount of reagent to get solution state. The quantity of the liquid specimen is 100 µl to 300 µl, more preferably around 200 µl. The quantity of the principal ingredients of the reagent may be naturally the required quantity to react the liquid specimen.

When this vial is set, for example, on an examination apparatus of toxinometer, the liquid level of the inside specimen can be elevated as the outer bottom plane is formed to be convex. In addition, since the inner bottom is formed to be the round-state convex part, the part between the round-state convex part and the meniscus part can be light irradiating part for optical examination even when quantity of the liquid specimen is in small amount. It is preferable that the light irradiation part is set at 2.5 mm to 3.5 mm in height from the bottom (0.3 mm to 1.8 mm from the top of the inner bottom plane, preferably 0.5 mm to 1.5 mm) in the straight part of the vial (no distortion exists). Light quantity examination is required to perform above the top end of the bottom part outer round part (curved part). Accordingly, even though the bottom is formed flat, the part of about 1 mm above the inner bottom flat plane cannot be light irradiation part, thereby when the bottom is formed to be a round-state convex part, quantity of the liquid specimen can be reduced.

Thereafter, light is irradiated toward bottle center to examine the light quantity variation in the opposite direction to the irradiation side.

The cell vial according to the present invention can be used for "examination of light quantity variation" without any hindrance, which is preferably used in a case where specimen is especially in small quantity, or where the consumption of reagent is required to decrease due to expensive price.

For example, since reagent for endotoxin examination (for example, LAL reagent) is expensive, it is preferable to use as less amount as possible and specially suitable to apply in the present invention.

Here, LAL stands for Amoebocyte Lysate extraction liquid (abridged to AL solution, hereinafter) of horseshoe crab in *Limulus* genus, which is specific reagent for endotoxin.

Endotoxin is lipopolysacharide which mainly exists in cell surface of gram-negative bacterium, which is known as a kind of Pyrogen. Accordingly, examination of endotoxin concentration in specimen is treated as an important element in the field of medical science, pharmacology, and microbiology.

At present as an examination method of this endotoxin, so-called *limulus* test, which utilizes coagulation phenomenon of AL solution through activation by endotoxin, is widely utilized considering points of simplicity, inexpensiveness and the like. AL solution which can be used in preparation method according to the present invention can include what is extraction from blood cell of horseshoe crab belonging to *Limulus* genus, *Tachypleus* genus, or *Carcinoscorplus* genus, and there is no limitation if it generates coagulation reaction in response to endotoxin. In addition, it is obvious that what is prepared based on freeze-dried substance of AL solution can be used, AL solution being available in the market through ACC Corporation (ASSOCIATES OF CAPE COD), Wako Chemicals USA, Cambrex Bio Science Walkersville, Endosafe, and the like.

The invention claimed is:

1. A manufacturing method of a glass tube for examining a specimen, comprising the steps of:
    holding a slender glass tube formed with an opening at a lower end of the glass tube for examining a specimen in the upright state;
    heating an upper end of the glass tube for examining a specimen with a burner while simultaneously rotating the glass tube for examining a specimen, and collecting melted glass at a central part of the upper end of the glass tube for examining a specimen to form a bottom of the glass tube for examining a specimen to be in a convex state upwardly or downwardly, and while simultaneously blowing in compressed air from the opening at the lower end of the glass tube for examining a specimen;
    varying the compressed air pressure so that an inner surface of the bottom of the glass tube for examining a specimen is formed to be a round-state convex part in a direction toward the opening at the lower end of the glass tube for examining a specimen, and an outer surface of the bottom of the glass tube for examining a specimen is formed to be in convex state in an opposite direction from the inner surface of the bottom of the glass tube for examining a specimen; and
    filling the glass tube for examining a specimen with a small quantity of reagent.

2. The manufacturing method according to claim 1, comprising the steps of:
- manufacturing the glass tube for examining a specimen having a thin bottom, a thin bottom being a bottom having a thickness equivalent to the thickness of an outer peripheral of the glass tube for examining a specimen, by heating with a burner and collecting melted glass at the central part of the upper end of the glass tube for examining a specimen; and
- subsequently, heating with a burner again to melt glass at the central part of the upper end of the glass tube for examining a specimen to form a thick bottom glass tube for examining a specimen, a thick bottom being a bottom having a thickness of 1.3 to 2 times that of the thin bottom, so that the inner surface of the bottom of the glass tube for examining a specimen is formed to be a round-state convex part in the direction toward the opening at the lower end of the glass tube for examining a specimen, and the outer surface of the bottom of the glass tube for examining a specimen is formed to be in a convex state in the opposite direction from the inner surface of the bottom of the glass tube for examining a specimen.

3. The manufacturing method according to claim 1, comprising the step of
- forming the outer surface of the bottom of the glass tube for examining a specimen to be a round-state convex part in the opposite direction from the inner surface of the bottom of the glass tube for examining a specimen.

* * * * *